United States Patent
Yurino et al.

(10) Patent No.: US 6,563,584 B1
(45) Date of Patent: May 13, 2003

(54) METHOD AND DEVICE FOR FLUORESCENCE MEASUREMENT

(75) Inventors: Noriko Yurino, Kanagawa (JP); Kenji Yamamoto, Kanagawa (JP); Kentaro Shishido, Kanagawa (JP)

(73) Assignee: Hitachi Software Engineering Co., Ltd., Yokohama (JP)

( * ) Notice: Subject to any disclaimer, the term of this patent is extended or adjusted under 35 U.S.C. 154(b) by 0 days.

(21) Appl. No.: 09/743,681

(22) PCT Filed: May 10, 2000

(86) PCT No.: PCT/JP00/02996

§ 371 (c)(1), (2), (4) Date: Mar. 15, 2001

(87) PCT Pub. No.: WO00/68668

PCT Pub. Date: Nov. 16, 2000

(30) Foreign Application Priority Data

May 11, 1999 (JP) ............................................. 11-129365

(51) Int. Cl.[7] .................................................. G01N 21/25
(52) U.S. Cl. ..................................................... 356/417
(58) Field of Search .................................. 356/402–425, 356/317–318, 73, 338, 244–246, 368; 250/458.1, 459.1, 461.1, 205, 584–585, 227.22, 328, 491.1, 361 C, 361 R, 461.2, 564, 227.23, 576, 227.31, 306; 436/172–174, 531, 86, 546, 63, 500, 527, 536, 47, 800; 422/102–104, 82.08, 63–67, 52, 82.05, 68.1; 435/173.4, 29, 287.1, 287.2, 288.1, 258.1, 6, 4, 7.1, 7.8, 91.2, 69.1

(56) References Cited

U.S. PATENT DOCUMENTS

| | | | | | |
|---|---|---|---|---|---|
| 4,626,684 | A | * | 12/1986 | Landa | 250/328 |
| 4,778,763 | A | * | 10/1988 | Makiguchi et al. | 250/459.1 |
| 5,397,709 | A | * | 3/1995 | Berndt | 356/442 |
| 5,993,746 | A | * | 11/1999 | Priha et al. | 356/244 |
| 6,042,785 | A | * | 3/2000 | Harju | 356/417 |
| 6,211,989 | B1 | * | 4/2001 | Wulf et al. | 356/317 |

FOREIGN PATENT DOCUMENTS

| | | |
|---|---|---|
| JP | 11-094747 | 9/1999 |
| WO | WO 94/02645 | 2/1994 |
| WO | WO 98/38495 | 9/1998 |
| WO | 98/38495 | * 9/1998 |

* cited by examiner

Primary Examiner—Tu T. Nguyen (57) ABSTRACT

The invention uses a continuous-wave laser as an excitation light source to achieve highly-accurate detection with a simple structure. A sample 11a is irradiated with excitation light from an excitation light source 30, and then transported to an optical axis of a fluorescence detector 50, thereby being detected of its fluorescence intensity.

15 Claims, 5 Drawing Sheets

PRIOR ART

METHOD AND DEVICE FOR FLUORESCENCE MEASUREMENT

CROSS-REFERENCES TO RELATED APPLICATIONS

The present application claims the benefit of priority under 35 U.S.C. §371 to Patent Convention Treaty (PCT) International Application Serial No: PCT/JP00/02996, filed May 10, 2000, and its priority document Japanese patent application serial number 129365/1999, filed May 11, 1999. These applications are explicitly incorporated herein by reference in their entirety and for all purposes.

1. Technical Field

The present invention relates to a method and a device for fluorescence measurement. More particularly, the present invention relates to a method and a device for fluorescence measurement which is favored for reading a biochip on which fluorescence-labeled samples such as DNAs or proteins are arranged in a plane.

2. Background Art

In the fields of molecular biology and biochemistry, hybridization reaction between a nucleic acid or a protein having a known sequence and a target molecule contained in a sample is employed for searching useful genes or for diagnosing diseases. For this purpose, a biochip is used which has a plurality of sample spots on its surface for processing a mass number of samples in a short time. Each sample spot on the biochip has a different probe immobilized thereon. This biochip is placed into a reaction vessel together with a sample DNA to hybridize probes bound to the sample spots on the biochip with the fluorescence-labeled sample DNA. Then, the biochip is irradiated with excitation light to measure the fluorescent intensity of each sample spot with a fluorescence measurement device. Accordingly, a binding level between each probe and the sample DNA is obtained, which is then converted into a desired piece of information.

Figure 5:
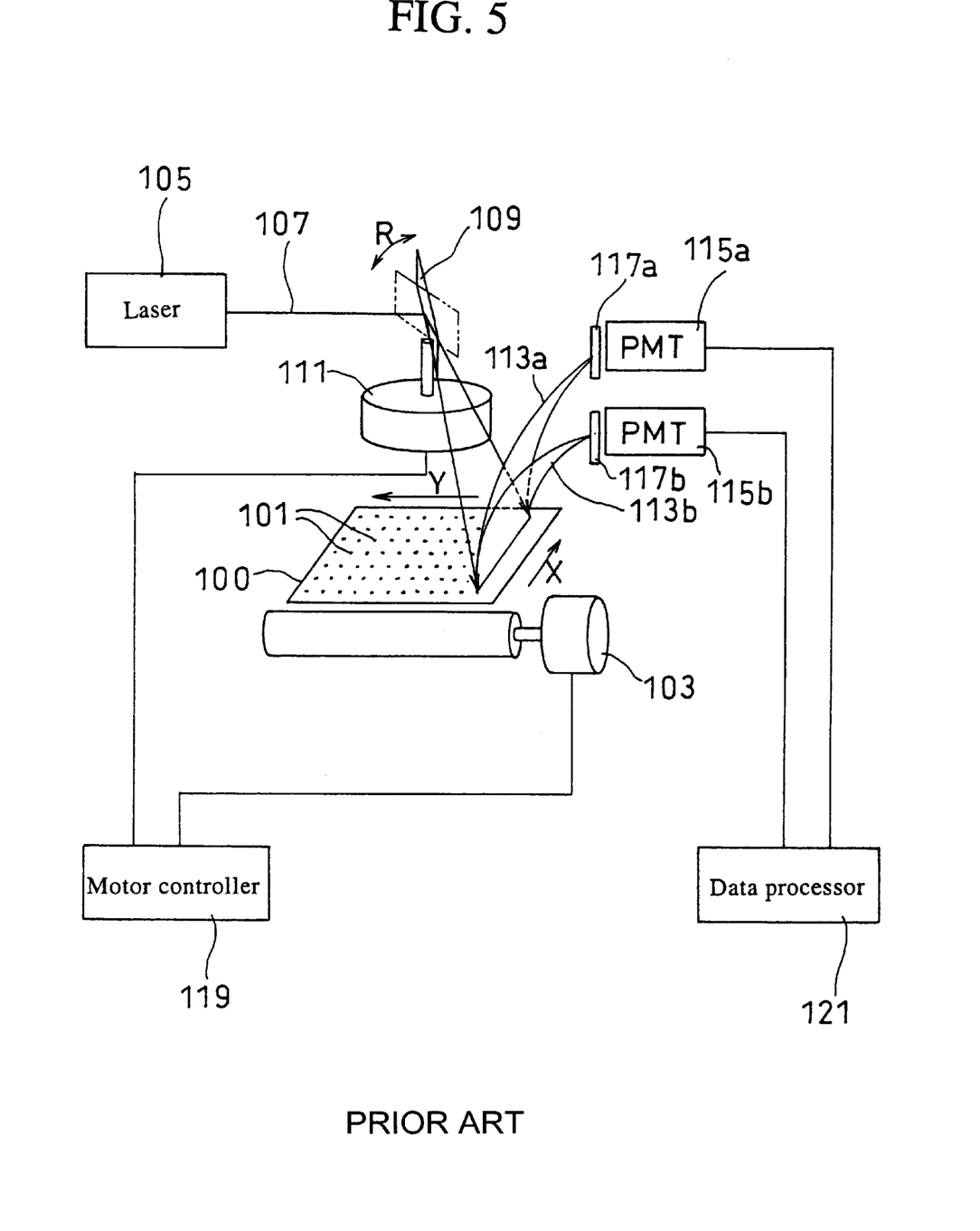
FIG. 5 is a schematic view showing a conventional fluorescence measurement device.

FIG. 5 is a schematic view showing a conventional fluorescence measurement device used for reading a biochip. The fluorescence measurement device radiates excitation light to each sample spot on the biochip and incorporates fluorescence emitted from each sample spot via an optical fiber bundle according to a luminous point scanning system.

The surface of the biochip 100 made of a slide glass or the like, has fluorescence-labeled sample spots 101 such as DNAs and proteins in a lattice arrangement. For example, microscopic spots with diameters of 50 μm are arranged placing a space of about 100 μm therebetween in a direction represented by an arrow Y. A chip-transporting motor 103 transports the biochip 100 in the parallel direction represented by the arrow Y. A laser beam 107 generated by a laser 105 reflects off a rotary mirror 109 and is guided to the surface of the biochip as a luminous point. The rotary mirror 109 is rotated by a motor 111 in a direction represented by an arrow R. The laser beam 107 linearly scans the surface of the biochip 100 in a direction represented by an arrow X. A motor controller 119 controls the chip-transporting motor 103 and the motor 111 as described above to run the laser beam in X-direction while continuously transporting the biochip in Y-direction to radiate the whole sample surface of the biochip 100.

The fluorescence emitted from each sample spot on the biochip is guided to photomultiplier tubes (PMTs) 115a and 115b via optical fiber bundles 113a and 113b, respectively. The incident ends of the optical fiber bundles 113a and 113b are arranged in lines corresponding to the scanning line of the laser beam on the surface of the biochip 100. The other ends of the optical fiber bundles 113a and 113b extend to the PMTs 115a and 115b, respectively. Optical filters 117a and 117b are provided between the optical fiber bundles 113a and 113b and the PMTs 115a and 115b, respectively, so that only the fluorescent wavelength of interest is read by the PMTs 115a and 115b. The output from the PMT 115a and 115b is sent to a data processor 121 for data processing. In this manner, a plurality of light receiving systems with optical filters of different wavelength transmitting ranges are provided to allow polychromatic reading.

The light receiving systems of the above-described conventional fluorescence measurement device receive not only the fluorescence from the sample but also excitation laser beam reflected or scattered off the sample surface. Since the amount of the sample is microscopic, the quantity of excitation light incident to the light receiving system is so many times greater than the quantity of the fluorescence incident to the same. Thus, the optical filter needs to have a narrow wavelength transmitting range to eliminate the excitation light, in which case the fluorescence that needs to be detected is often cut-off as well. Since the number of the optical fiber bundles used for incorporating fluorescence needs to satisfy at least the number of the samples along the beam scanning direction, it is disadvantageous in terms of cost and it requires precise mechanism and adjustment for aligning optical axes.

Furthermore, since the light-receiving angle of the optical fibers is small and thus small amount of fluorescence is incorporated from the sample, an S/N ratio tends to be low. In order to increase the S/N ratio, there has been an attempt to receive only the fluorescence from the sample by using a pulsed laser and acoustooptic modulator (AOM) to attenuate the intensity of the excitation laser beam immediately after exciting the sample. However, pulsed lasers are expensive, and AOM merely attenuates the intensity of the laser beam by $1/1000$ and cannot completely prevent the excitation laser beam from contaminating.

DISCLOSURE OF INVENTION

The aim of the present invention is to solve the above-described problems concerned with the conventional technique and to provide a method and a device for fluorescence measurement with high detection accuracy with a simple structure by using a relatively inexpensive laser such as a continuous-wave laser (CW laser) as an excitation light source.

According to the present invention, an excitation light radiating section and a fluorescence detecting section are provided spatially separated from each other. The sample irradiated with excitation light at the excitation light radiating section is transported to the fluorescence detecting section so that the fluorescence can be detected without being interrupted by the excitation light. Accordingly, an S/N ratio is enhanced and thus the above-described aim can be accomplished.

A method for fluorescence measurement of the invention comprises the steps of: irradiating a sample with excitation light from an excitation light source; transporting the sample irradiated with excitation light to an optical axis of a fluorescence detector; and detecting fluorescence incident on the fluorescence detector. The sample comprises a biopolymer labeled with a fluorescent substance.

According to this method, the sample irradiated with excitation light is transported, within a time shorter than the duration time of the fluorescence emitted from the sample, to an optical axis of the fluorescence detector, the optical axis directing towards a position shifted from the excitation light irradiation position. Since the excitation light reflected or scattered off the sample at the excitation light irradiation position is not incident upon the fluorescence detector, only the fluorescence may be detected with high sensitivity.

A device for fluorescence measurement according to the present invention comprises: an excitation light source; an excitation light radiating means for irradiating a sample with excitation light from the excitation light source; a fluorescence detector for detecting fluorescence emitted from the sample irradiated with excitation light, the fluorescence detector having an optical axis that does not, above the sample, cross with an optical axis of the excitation light radiating means; and a sample transporting means for transporting the sample irradiated with the excitation light of the excitation light radiating means to the optical axis of the fluorescence detector.

In the device for fluorescence measurement, an optical axis of an excitation light radiating means and an optical axis of a fluorescence detector do not cross with each other. The fluorescence of the sample is not measured under the excitation light radiating means but after the sample is transported to the fluorescence detector within a time shorter than the duration time of the fluorescence. By spatially separating the fluorescence irradiation position from the fluorescence detecting position, the excitation light reflected or scattered off the sample at the excitation light irradiation position is not incident upon the fluorescence detector. As a result, only the fluorescence can be detected with high sensitivity.

Preferably, the fluorescence detector is provided with a photodetector such as PMT and a confocal optical system in which the photodetecting surface of the photodetector and the sample surface are conjugate. The sample transporting means may rotatively transport the sample. A plurality of sets of excitation light sources, excitation light radiating means and fluorescence detectors may be provided for detecting fluorescence of different wavelengths.

The fluorescent substance used with the present invention preferably has long fluorescence duration time and preferably is an Eu (europium) complex such as 4,4'-bis(1",1",1", 2",2",3",2"-heptafluoro-4",6"-hexanedion-6"-yl) chlorosulfo-o-terphenyl (BHHCT), rhodamine, FITC, Cy3 and Cy5. For example, BHHCT is a fluorescent substance which emits fluorescence with a wavelength of 615 nm as irradiated with a wavelength of 340 nm, and which has a fluorescent half-life of 100–200 $\mu$sec which is very long compared to those of conventional fluorescent substances (which are several tens of nsec). By utilizing this property, a high level of fluorescence can be obtained upon irradiating the sample with excitation light and transporting the sample for fluorescence detection, thereby dramatically enhancing an S/N ratio.

BEST MODE FOR CARRYING OUT THE INVENTION

Hereinafter, the present invention will be described in detail with reference to the drawings.

Figure 1:
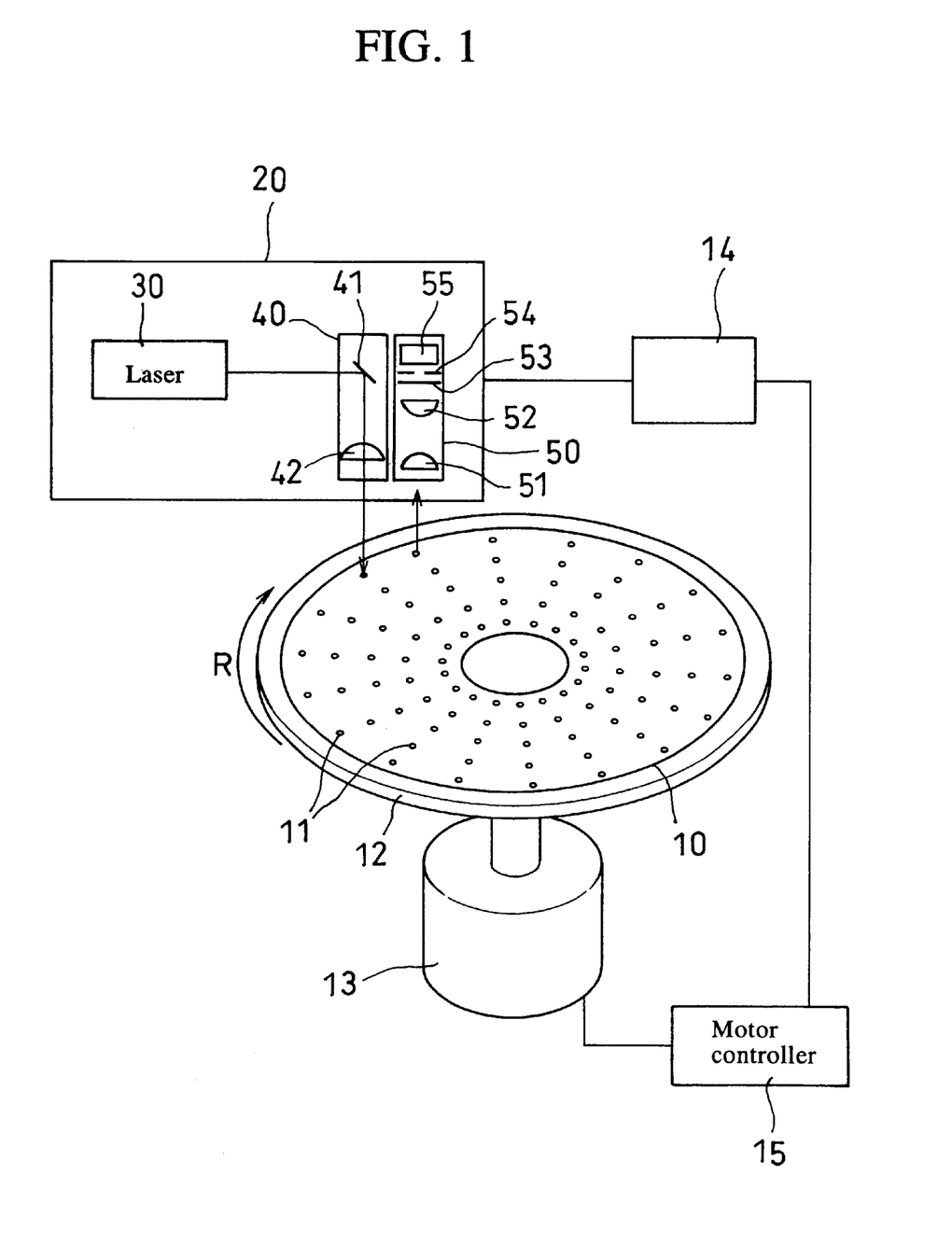
FIG. 1 is a schematic view showing an exemplary fluorescence measurement device according to the invention.

FIG. 1 is a schematic view showing an exemplary fluorescence measurement device according to the invention. This device is suitable for reading a circular biochip. The circular biochip 10 is provided with a plurality of sample spots 11 arranged in concentric circles or in a spiral. The biochip 10 is held on a sample platform 12 which may be rotatively driven in a direction represented by an arrow R by a rotating motor 13. Above the biochip 10 is provided an optical head 20 having an excitation light source 30, an excitation light radiating optical system 40 and a fluorescence detecting optical system 50. For example, on the sample spots 11 which are as microscopic as 50 $\mu$m in diameter, a biopolymer such as DNA or a protein labeled with fluorescent substance is hybridized with probe DNAs or the like.

The excitation light source 30 may be, for example, a continuous-wave (CW) laser. The laser beam emmited from the excitation light source 30 is incident on the excitation light radiating optical system 40, reflected off a mirror 41, converged by an object lens 42 towards the sample spots on the biochip 10. The fluorescence detecting optical system 50 is provided with a light receiving lens 51, a converging lens 52, a fluorescence selection filter 53, a slit 54 and a photomultiplier tube as a photodetector 55, to detect the fluorescence from the sample spots.

The optical head 20 is transported and aligned by a head transporting motor 14 in the radial direction of the biochip 10. When the sample spots 11 are arranged in concentric circles on the biochip 10, the head transporting motor 14 stepwisely aligns the optical head 20 with respect to each concentric circle of the sample spots. When the sample spots 11 are arranged in a spiral on the biochip 10, the head transporting motor 14 continuously transports the optical head 20 to chase the spirally-arranged sample spots 11. A motor controller 15 controls the rotating motor 13 and the head transporting motor 14 to adjustably control the rotational speed of the rotating motor 13 according to the radial position of the optical head 20 on the biochip 10 such that the transporting rate of the sample spots 11 under the optical head 20 is always generally constant.

Figure 2A:
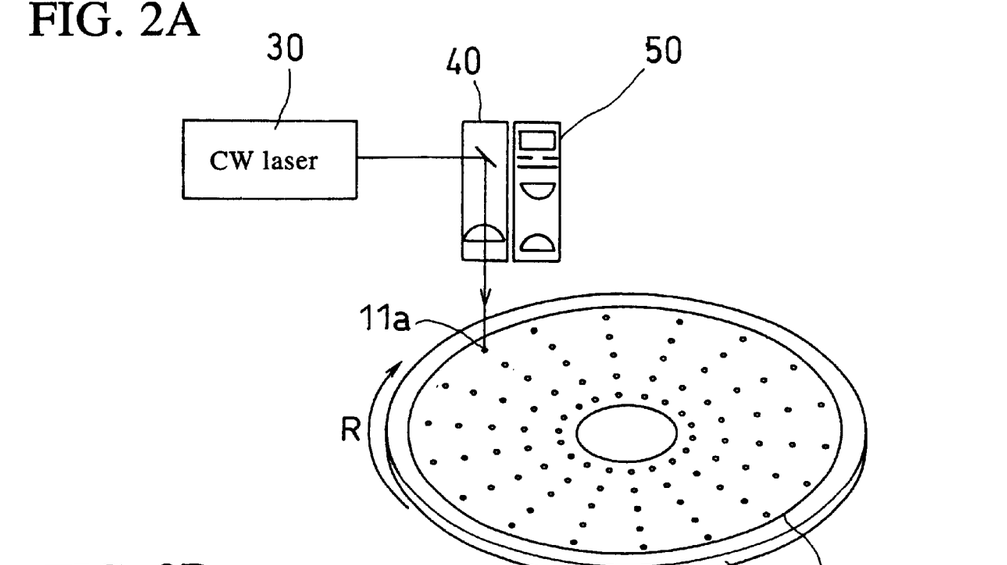
FIGS. 2A and 2B are schematic views for illustrating the positional relationship between an excitation light radiating optical system and a fluorescence detecting optical system.
Figure 2B:
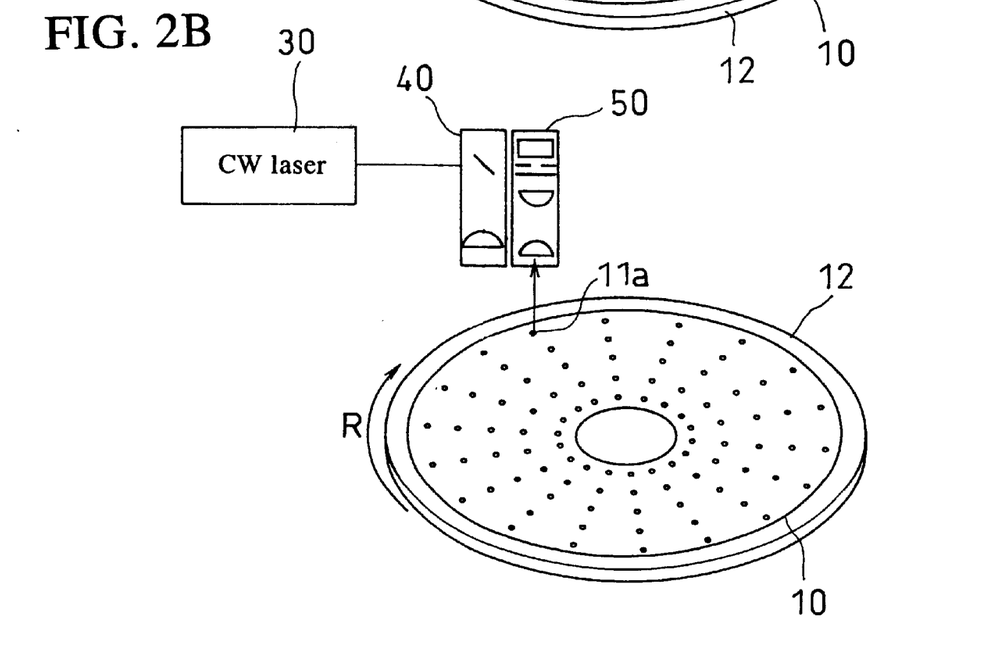

FIGS. 2A and 2B are schematic views for illustrating the positional relationship between the excitation light radiating optical system and the fluorescence detecting optical system. Referring to FIG. 2A, one of the sample spots 11 on the rotating biochip 10 is irradiated with excitation light from the excitation light source (CW laser) 30 via the excitation light radiating optical system 40 to excite the fluorescent substance contained in the sample spot 11a. Thereafter, as shown in FIG. 2B, the sample spot 11a irradiated with excitation light is transported as the biochip 10 rotates to come directly under the fluorescence detecting optical system 50. At this position, the fluorescence emitted from the sample spot 11a is incident on and detected by the fluorescence detecting optical system 50.

Figure 3A:
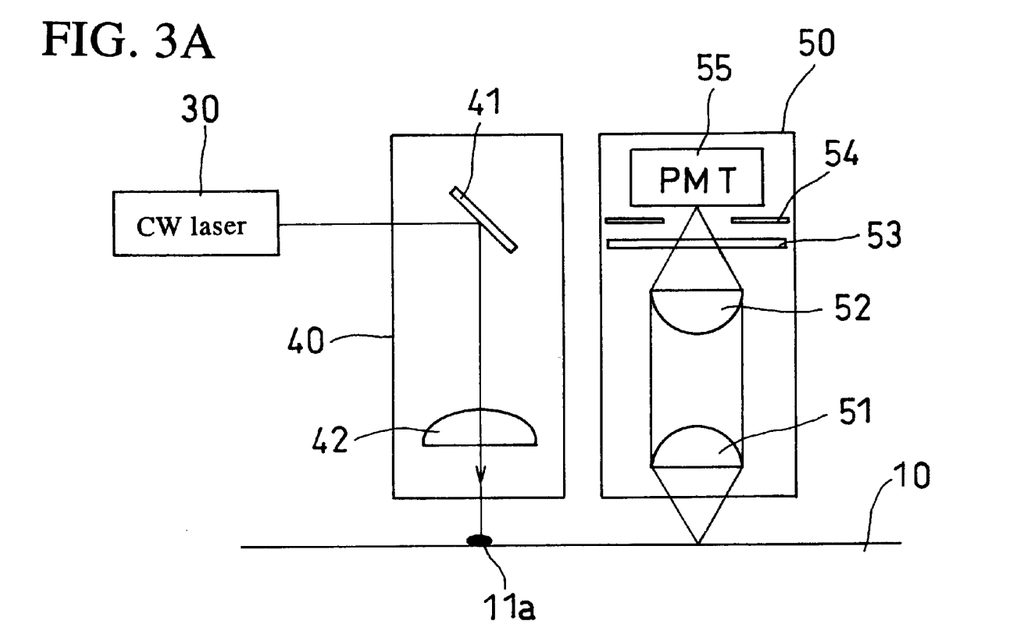
FIGS. 3A and 3B are schematic views for illustrating the principle of fluorescence detection according to the invention.
Figure 3B:
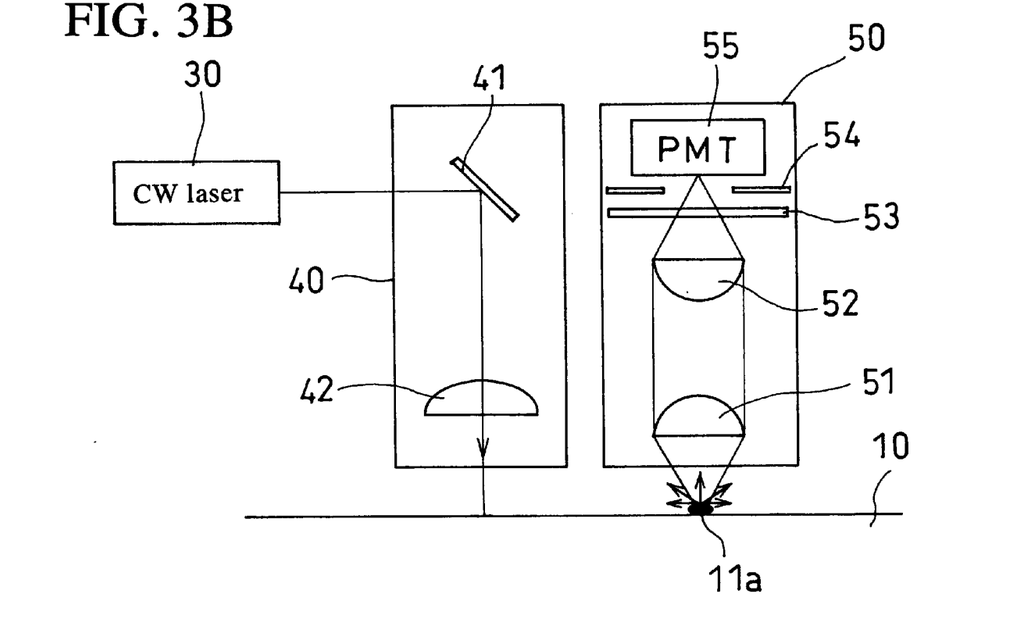

FIGS. 3A and 3B are schematic views for illustrating the principle of the fluorescence detection according to the present invention. FIG. 3A shows the state where the sample spot 11a on the transporting biochip 10 is being irradiated with excitation light from the CW laser 30. If the sample spot 11a contains a fluorescence label substance, the sample spot 11a irradiated with the excitation light will emit fluorescence. The sample spot that has been irradiated with the excitation light will pass under the excitation light radiating optical system 40, and a predetermined time after the irradiation, will come under the fluorescence detecting optical system 50 as shown in FIG. 3B. The light receiving lens 51 and the converging lens 52 of the fluorescence detecting optical system 50 form a confocal optical system. The fluorescence emitted from the sample spot 11a scatters in every direction while the fluorescence incident upon the light receiving lens 51 forming the confocal optical system will be converged by the converging lens 52. The converged fluorescence passes through the optical filter 53 and the slit 54 for noise elimination and is incident on the a photodetector (PMT) 55, thereby being detected. Accordingly, fluorescence can be detected without being interrupted by the excitation light. Although the optical axis of the excitation light radiating optical system 40 and the optical axis of the fluorescence detecting optical system 50 are shown parallel to each other in the figure, the optical axes of the two optical systems 40 and 50 may not necessarily be parallel.

Figure 4:
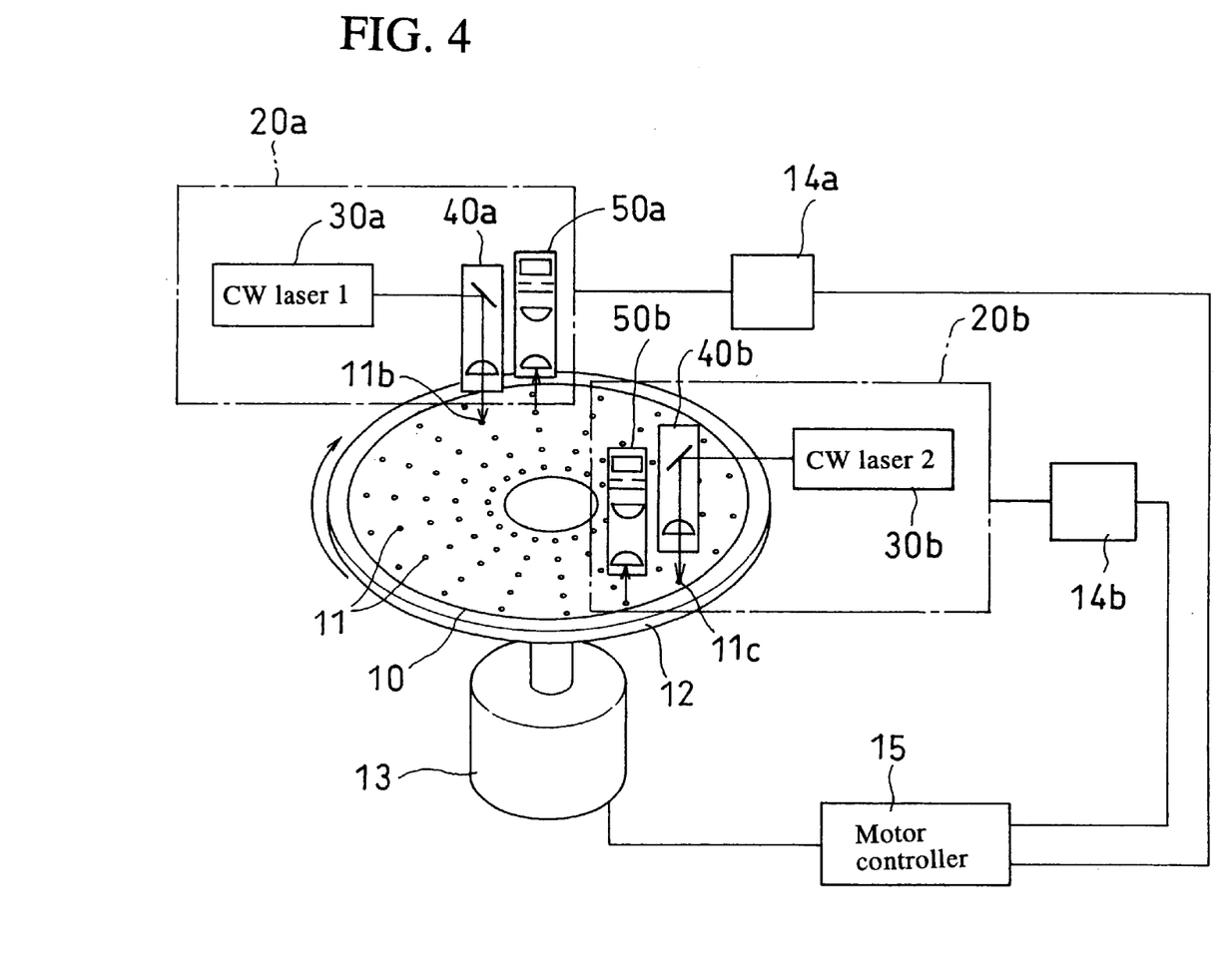
FIG. 4 is a schematic view showing another exemplary fluorescence measurement device according to the invention.

FIG. 4 is a schematic view for illustrating another example of a fluorescence measurement device of the invention. The fluorescence measurement device is provided with two optical heads 20a and 20b for identifying and detecting fluorescence from two types of fluorescent substances contained in sample spots. The optical head 20a is provided with an excitation light source (CW laser) 30a, an excitation light radiating optical system 40a and a fluorescence detecting optical system 50a. The optical head 20b is provided with an excitation light source (CW laser) 30b, an excitation light radiating optical system 40b and a fluorescence detecting optical system 50b. The structures of the excitation light radiating optical systems 40a and 40b and the fluorescence detecting optical systems 50a and 50b are identical to those of the excitation light radiating optical system 40 and the fluorescence detecting optical system 50 shown in FIG. 1, respectively, and thus description of the details thereof is omitted.

The excitation light sources 30a and 30b are respectively provided with optical filters so that excitation wavelengths can be selected for efficiently exciting different fluorescent substances. The fluorescence detecting optical systems 50a and 50b are respectively provided with optical filters so that wavelength transmitting ranges can be selected for efficiently detecting fluorescence from different fluorescent substances. One optical head 20a radiates excitation light from the excitation light source 30a to a sample spot 11b via the excitation light radiating optical system 40a. After a prescribed time, fluorescence emitted from the sample spot 11b is measured by the fluorescence detecting optical system 50a without being interrupted by the excitation light, for example, to selectively detect Cy3 contained in the sample spot 11b. The other optical head 20b radiates excitation light from the excitation light source 30b to a sample spot 11c via the excitation light radiating optical system 40b. After a prescribed time, fluorescence emitted from the sample spot 11c is measured by the fluorescence detecting optical system 50b without being interrupted by the excitation light, for example, to selectively detect Cy5 contained in the sample spot 11c.

The two optical heads 20a and 20b are transported by head transporting motors 14a and 14b, respectively, in the radial direction of the biochip 10 to be aligned generally at the same radial distances. When the sample spots 11 are arranged in concentric circles on the biochip 10, the head transporting motors 14a and 14b stepwisely aligns the optical heads 20a and 20b with respect to each concentric circle of the sample spots. When the sample spots 11 are arranged in a spiral on the biochip 10, the head transporting motors 14a and 14b continuously transport the optical heads 20a and 20b to chase the spirally-arranged sample spots 11. A motor controller 15 controls the rotating motor 13 and the head transporting motors 14a and 14b to adjustably control the rotational speed of the rotating motor 13 according to the radial positions of the optical heads 20a and 20b on the biochip 10 such that the transporting rate of the sample spots 11 under the optical heads 20a and 20b is almost generally constant.

Industrial Applicability

According to the present invention, fluorescence from a fluorescent substance contained in a sample spot may be measured with high sensitivity without being interrupted by excitation light.

What is claimed is:

1. A fluorescence measurement device comprising:

a sample platform mounting a circular biochip, wherein the circular biochip comprises sample spots arranged in concentric circles or in a spiral;

a first motor for rotating the sample platform;

an optical head comprising an excitation light radiating optical system and a fluorescence detecting optical system;

a second motor for driving the optical head relatively in a radial direction of the sample platform; and a motor controller for controlling the first and second motors, wherein the excitation light radiating optical system and the fluorescence detecting optical system are disposed such that their optical axes do not cross one another above a sample spot to be measured, and the sample spot irradiated by the excitation light radiating optical system comes immediately below the fluorescence detecting optical system as the sample platform is rotated by the first motor, and the motor controller controls the rotational speed of the first motor in accordance with the radial position of the optical head over the sample platform such that the transporting rate of the sample spots under the optical head is generally constant.

2. The fluorescence measurement device of claim 1, wherein the sample spots are formed by a biopolymer labeled with a fluorescent substance.

3. The fluorescence measurement device of claim 2, wherein the fluorescent substance is selected from the group consisting of Cy3, Cy5, FITC, rhodamine and BHHCT.

4. The fluorescence measurement device of claim 1, wherein the second motor transports the optical head in a stepwise manner.

5. The fluorescence measurement device of claim 1, wherein the second motor transports the optical head continuously.

6. The fluorescence measurement device of claim 1, wherein the fluorescence measurement device comprises a plurality of optical heads.

7. The fluorescence measurement device of claim 6, wherein the plurality of optical heads are capable of detecting fluorescence of different wavelengths.

8. The fluorescence measurement device of claim 1, wherein the fluorescence detecting optical system comprises a photodetector and a confocal optical system.

9. The fluorescence measurement device of claim 1, wherein the excitation light radiating optical system comprises an excitation light source comprising a laser.

10. The fluorescence measurement device of claim 9, wherein the laser comprises a continuous-wave (CW) laser.

11. A fluorescence measurement device comprising:
   (a) a sample platform;
   (b) a biochip comprising a plurality of sample spots arranged in concentric circles or in a spiral pattern, wherein the biochip is held on the sample platform;
   (c) a motor for rotating the sample platform;
   (d) an optical head comprising an excitation light source and a fluorescence detecting optical system;
   (e) a motor for driving the optical head in a radial direction of the sample spots on the sample platform; and
   (f) a controller for controlling the sample platform motor and the optical head motor, wherein the controller controls the rotational speed of the sample platform motor in accordance with the radial position of the optical bead over the sample platform such that the transporting rate of the sample spots under the optical head is constant,
      and the excitation light source and the fluorescence detecting optical system are disposed such that their optical axes do not cross one another above a sample spot,
      and the sample spot irradiated by the excitation light source is positioned immediately below the fluorescence detecting optical system as the sample platform is rotated.

12. A fluorescence measurement device comprising:
   (a) a sample platform and a biochip, wherein the biochip comprises a plurality of sample spots arranged in concentric circles or in a spiral pattern and the biochip is held on the sample platform;
   (b) a rotating means for rotating the sample platform;
   (c) an optical head comprising an excitation light radiating optical system and a fluorescence detecting optical system;
   (d) a means for driving the optical head in a radial direction of the sample platform; and
   (e) a controlling means for controlling the sample platform rotating means and the optical head driving means, wherein the controlling means controls the rotational speed of the sample platform rotating means in accordance with the radial position of the optical head over the sample platform such that the transporting rate of the sample spots under the optical head is generally constant,
      and the excitation light radiating optical system and the fluorescence detecting optical system are disposed such that their optical axes do not cross one another above a sample spot,
      and the sample spot irradiated by the excitation light radiating optical system is positioned immediately below the fluorescence detecting optical system as the sample platform is rotated.

13. A fluorescence measurement device comprising:
   (a) a circular biochip comprising a plurality of sample spots arranged in concentric circles or in a spiral pattern;
   (b) a rotating means for rotating the circular biochip;
   (c) an optical head comprising an excitation light radiating optical system and a fluorescence detecting optical system;
   (d) a means for driving the optical head in a radial direction of the circular biochip; and
   (e) a controlling means for controlling the circular biochip rotating means and the optical head driving means, wherein the controlling means controls the rotational speed of the circular biochip in accordance with the radial position of the optical head over the circular biochip such that the transporting rate of the sample spots under the optical head is generally constant,
      and the excitation light radiating optical system and the fluorescence detecting optical system are disposed such that their optical axes do not cross one another above a sample spot,
      and the sample spot irradiated by the excitation light radiating optical system is positioned immediately below the fluorescence detecting optical system as the circular biochip is rotated.

14. A fluorescence measurement device comprising:
   (a) a sample platform and a biochip, wherein the biochip comprises a plurality of sample spots arranged in concentric circles or in a spiral pattern and the biochip is held on the sample platform;
   (b) a motor for rotating the sample platform;
   (c) an optical head comprising an excitation light source comprising a continuous-wave (CW) laser and a fluorescence detecting optical system;
   (d) a motor for driving the optical head in a radial direction of the sample platform; and
   (e) a motor controller for controlling the sample platform motor and the optical head motor, wherein the motor controller controls the rotational speed of the sample platform motor in accordance with the radial position of the optical head over the sample platform such that the transporting rate of the sample spots under the optical head is generally constant, and that a sample spot irradiated by the excitation light source is positioned immediately below the fluorescence detecting optical system as the sample platform is rotated,
      and the excitation light source and the fluorescence detecting optical system are disposed such that their optical axes do not cross one another above a sample spot.

15. A method for making a fluorescence measurement comprising the following steps:
   (a) providing a fluorescence measurement device which comprises:
      a sample platform mounting a circular biochip, wherein the circular biochip comprises sample spots arranged in concentric circles or in a spiral;
      a first motor for rotating the sample platform;
      an optical head comprising an excitation light radiating optical system and a fluorescence detecting optical system;
      a second motor for driving the optical head relatively in a radial direction of the sample platform; and
      a motor controller for controlling the first and second motors,
      wherein the excitation light radiating optical system and the fluorescence detecting optical system are disposed such that their optical axes do not cross one another above a sample spot to be measured, and the sample spot irradiated by the excitation light radiating optical system comes immediately below the fluorescence detecting optical system as the sample platform is rotated by the first motor;

(b) providing a sample;

(c) applying the sample of step (b) to the biochip of Step (a);

(d) irradiating the sample on the biochip with the excitation light radiating optical system;

(e) rotating the sample platform of step (a) to position the irradiated sample immediately below the fluorescence detecting optical system, wherein the rotational speed of the sample platform motor is controlled in accordance with the radial position of the optical head over the sample platform such that the transporting rate of the sample spots under the optical head is relatively constant; and (f) detecting the fluorescence emitted from the sample, thereby making the fluorescence measurement.

* * * * *